US005667806A

United States Patent [19]
Kantor

[11] Patent Number: 5,667,806
[45] Date of Patent: Sep. 16, 1997

[54] SPRAY DRYING METHOD AND APPARATUS

[75] Inventor: Martin L. Kantor, Mamaroneck, N.Y.

[73] Assignee: Emisphere Technologies, Inc., Hawthorne, N.Y.

[21] Appl. No.: 475,882

[22] Filed: Jun. 7, 1995

[51] Int. Cl.⁶ .................. A61K 9/16; A61K 9/50
[52] U.S. Cl. .............. 424/484; 424/485; 424/486; 424/489; 424/490; 424/491; 424/497; 424/499; 264/4.1; 264/4.3; 264/4.33
[58] Field of Search ................... 424/484, 485, 424/486, 489, 490, 491, 497, 499; 264/4.1, 4.3, 4.33

[56] References Cited

U.S. PATENT DOCUMENTS

| Re. 24,899 | 11/1960 | Green. | |
|---|---|---|---|
| 2,671,451 | 3/1954 | Bolger | 128/260 |
| 2,862,918 | 12/1958 | Meyer et al. | 260/123.5 |
| 2,868,740 | 1/1959 | Luce | 260/8 |
| 2,971,916 | 2/1961 | Schleicher et al. | 252/62.5 |

(List continued on next page.)

FOREIGN PATENT DOCUMENTS

| 1077842 | 8/1976 | Canada. |
|---|---|---|
| 0 000 667 A1 | 2/1979 | European Pat. Off.. |
| 0 036 145 A1 | 9/1981 | European Pat. Off.. |
| 0 068 314 | 1/1983 | European Pat. Off.. |
| 0 105 804 | 4/1984 | European Pat. Off.. |
| 0 130 162 A2 | 1/1985 | European Pat. Off.. |
| 0 170 540 A1 | 2/1986 | European Pat. Off.. |
| 0 342 054 A2 | 11/1989 | European Pat. Off.. |
| 0 342 056 A2 | 11/1989 | European Pat. Off.. |
| 0 365 183 | 4/1990 | European Pat. Off.. |
| 0 366 277 | 5/1990 | European Pat. Off.. |
| 0 418 642 | 3/1991 | European Pat. Off.. |
| 0 448 057 | 9/1991 | European Pat. Off.. |
| 0 452 161 | 10/1991 | European Pat. Off.. |
| 0 459 795 | 12/1991 | European Pat. Off.. |
| 0 467 389 | 1/1992 | European Pat. Off.. |
| 0 490 549 A1 | 6/1992 | European Pat. Off.. |
| 0 517 211 A1 | 9/1992 | European Pat. Off.. |
| 0 616 799 A1 | 9/1994 | European Pat. Off.. |
| 1 351 358 | 3/1964 | France. |
| 1 468 601 | 2/1967 | France. |
| 2 133 926 | 12/1972 | France. |
| 2 326 934 | 5/1977 | France. |
| 2 565 102 | 12/1985 | France. |
| 929401 | 6/1963 | Germany. |
| 1075952 | 8/1967 | Germany. |
| 2 424 169 | 12/1974 | Germany. |
| 3 202 255 | 10/1982 | Germany. |
| 3 612 102.9 | 10/1986 | Germany. |
| 71258/2 | 12/1987 | Israel. |
| 48-24246 | of 1973 | Japan. |
| 56-68612 | 6/1981 | Japan. |
| 58-35111 | of 1983 | Japan. |
| 280825 | 12/1964 | Netherlands. |
| 280826 | 12/1964 | Netherlands. |
| B-146698 | 11/1982 | Norway. |
| 1 567 763 | 5/1980 | United Kingdom. |
| 2 095 994 | 10/1982 | United Kingdom. |
| WO 85/02772 | of 0000 | WIPO. |
| WO 85/00105 | 1/1985 | WIPO. |
| WO85/00110 | 1/1985 | WIPO. |
| WO 87/04076 | 7/1987 | WIPO. |
| WO 88/01213 | 2/1988 | WIPO. |
| WO 92/19263 | 12/1992 | WIPO. |
| WO 93/18754 | 9/1993 | WIPO. |
| WO 93/25583 | 12/1993 | WIPO. |
| WO 94/14420 | 7/1994 | WIPO. |
| WO 94/18950 | 9/1994 | WIPO. |
| WO 94/18997 | 9/1994 | WIPO. |
| WO 94/21234 | 9/1994 | WIPO. |
| WO 94/23702 | 10/1994 | WIPO. |
| WO 94/23767 | 10/1994 | WIPO. |
| WO 94/24291 | 10/1994 | WIPO. |
| WO 94/28878 | 12/1994 | WIPO. |
| WO 95/11690 | 5/1995 | WIPO. |

OTHER PUBLICATIONS

Airaudo, C.B. et al. (1987) *Journal of Food Science*, vol. 52(6), pp. 1750–1752.
Andini, S. et al. (1975) *Origins of Life*, vol. 6, pp. 147–153.
Brooke, S. 1 et al. (1977) *BioSystems*, vol. 9, pp. 1–22.
Chen et al. (1975) "Evidence for Hemiacetal Formation", *Biochemistry*, vol. 18, No. 5, pp. 921–925.
Davis et al. (1983) "Leucinal Inhibits . . . ", *Pharmacology Biochemistry Behavior*, vol. 19, pp. 791–794.
Dose, K. (1974) *Origins of Life*, vol. 5, pp. 239–252.
Fasman et al. (1964) *Biochemistry*, vol. 3, No. 11, pp. 1665–1674.
Fox, S.W. et al. (1976) *BioSystems*, vol. 8, pp. 40–44.
Fox, S.W. et al., *Molecular Evolution and the Origin of Life*, Maxel Decker, New York (1977).
Fox, S.W.. (1976) *Origins of Life*, vol. 7, pp. 49–68.
Fox, S.W. (1980) *Naturwissenschaften*, vol. 67, pp. 378–383.
Fox, S.W. et al. (1960) *Archives of Biochemistry and Biophysics*, vol. 86, pp. 281–285.
Fox, S.W. et al. (1974) *Origins of Life*, vol. 5, pp. 227–237.
Fox, S.W. (1984) *Origins of Life*, vol. 14, pp. 485–488.
Gol'dovskii, A.M. (1978) *Zhurnal Evolyutsionnoi Biokhimii i Fiziologii*, vol. 14(6), pp. 437–439.
Gurrieri, S. et al,. (1973) *Thermochimica Acta*, vol. 7, pp. 231–239.
Harada, K. et al. (1979) *BioSystems*, vol. 11, pp. 47–53.
Harada et al., (1960) *Archives of Biochemistry and Biophysics*, vol. 86, pp. 274–280.
Hare (1970) *Etude Cenetique De La Polycondensaaon Thermique D'$_x$-Amino Acides*, vol. 45, pp. 330–339.
Heinrich, M.R. et al. (1969) *Archives of Biochemistry and Biophysics*, vol. 130, pp. 441–448.

(List continued on next page.)

*Primary Examiner*—Nathan M. Nutter
*Attorney, Agent, or Firm*—Darby & Darby

[57] ABSTRACT

Methods for preparing microspheres are provided. A carrier vehicle and a precipitator are nebulized and contacted. Alternatively, a carrier is nebulized in an aqueous acid and the concentration of the acid is decreased. Apparatus are also provided.

**38 Cla

U.S. PATENT DOCUMENTS

| Number | Date | Name | Class |
|---|---|---|---|
| 3,016,308 | 1/1962 | Macaulay | 177/37 |
| 3,052,655 | 9/1962 | Fox et al. | 260/78 |
| 3,057,344 | 10/1962 | Abella et al. | 128/2 |
| 3,076,790 | 2/1963 | Fox et al. | 260/78 |
| 3,170,802 | 2/1965 | Fukushima | 99/145 |
| 3,190,837 | 6/1965 | Brynko et al. | 252/316 |
| 3,474,777 | 10/1969 | Figge et al. | 128/2 |
| 3,491,093 | 1/1970 | Pachter et al. | 260/247.5 |
| 3,565,559 | 2/1971 | Sato | 424/37 |
| 3,567,650 | 3/1971 | Bakan | 252/316 |
| 3,574,832 | 4/1971 | Engel et al. | 424/183 |
| 3,576,758 | 4/1971 | Emrick | 252/316 |
| 3,725,113 | 4/1973 | Chang | 117/82 |
| 3,748,277 | 7/1973 | Wagner | 252/316 |
| 3,794,561 | 2/1974 | Matsukawa et al. | 195/29 R |
| 3,795,739 | 3/1974 | Birkmayer et al. | 424/274 |
| 3,822,348 | 7/1974 | Higashi et al. | 424/95 |
| 3,849,550 | 11/1974 | Teitelbaum | 424/78 |
| 3,937,668 | 2/1976 | Zolle | 252/316 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 3,976,773 | 8/1976 | Curran | 424/250 |
| 4,035,507 | 7/1977 | Bodor et al. | 424/311 |
| 4,048,268 | 9/1977 | Ludwig | 264/15 |
| 4,061,466 | 12/1977 | Sjoholm et al. | 23/230 B |
| 4,117,801 | 10/1978 | Dannelly et al. | 118/20 |
| 4,147,767 | 4/1979 | Yapel | 424/22 |
| 4,183,849 | 1/1980 | Hansen | 260/112.7 |
| 4,199,561 | 4/1980 | Roth et al. | 424/32 |
| 4,217,370 | 8/1980 | Rawlings et al. | 426/98 |
| 4,272,506 | 6/1981 | Schwarzberg | 424/8 |
| 4,289,759 | 9/1981 | Heavner et al. | 424/177 |
| 4,345,588 | 8/1982 | Widder et al. | 128/1.3 |
| 4,348,384 | 9/1982 | Horikoshi et al. | 424/101 |
| 4,351,337 | 9/1982 | Sidman | 128/260 |
| 4,352,883 | 10/1982 | Lim | 435/178 |
| 4,357,259 | 11/1982 | Senyei et al. | 252/316 |
| 4,388,304 | 6/1983 | Nyeki et al. | 424/177 |
| 4,402,856 | 9/1983 | Schnoring et al. | 428/402.22 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,690,786 | 9/1987 | Ninomiya et al. | 424/497 |
| 4,692,284 | 9/1987 | Braden | 264/4.3 |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/12 |
| 4,919,939 | 4/1990 | Baker | 424/493 |
| 4,925,673 | 5/1990 | Steiner | 424/455 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,019,400 | 5/1991 | Gombotz et al. | 424/490 |
| 5,039,481 | 8/1991 | Pacifici et al. | 422/4 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 424/70 |
| 5,250,236 | 10/1993 | Gasco | 264/4.4 |
| 5,271,934 | 12/1993 | Goldberg et al. | 424/490 |
| 5,271,961 | 12/1993 | Mathiowitz et al. | 427/213.31 |
| 5,278,148 | 1/1994 | Branca et al. | 514/19 |
| 5,328,992 | 7/1994 | Peter et al. | 534/116 |
| 5,352,461 | 10/1994 | Feldstein et al. | 424/493 |
| 5,389,379 | 2/1995 | Dirix et al. | 424/451 |

OTHER PUBLICATIONS

Heinz, B. et al. (1981) *BioSystems*, vol. 14, pp. 33–40.
Hennon, G. et al. (1975) *Biochimie*, vol. 57, pp. 1395–1396.
Hsu, L.L. et al. (1976) *BioSystems*, vol. 8, pp. 89–101.
Hsu, L.L. et al. (1971) *Currents in Modern Biology*, vol. 4, pp. 12–25.
Ishima, Y. et al. (1981), *BioSystems*, vol. 14, pp. 243–251.
Jackson et al. (1991) "Pharmacological . . . ", *J. Pharm. & Exp. Thera.*, vol. 261, No. 1, pp. 546–552.
Kokufuta, E. et al. (1984) *BioSystems*, vol. 16, pp. 175–181.
Jungck, J.R. et al. (1973) *Naturwissenschaten*, vol. 60, pp. 425–427.
Krampitz, G. et al,. (1967) *Naturwissenschaften*, pp. 516–517.
Krampitz, G. et al. (1968) *Naturwissenschaften*, pp. 345 and 346.
Krampitz, G. et al. (1966) *Naturwissenschaften*, pp. 7 and 8.
Lacey, Jr., J.C. et al. (1979) *BioSystems*, vol. 11, pp. 9–17.
Lacey, Jr., J.C. et al. (1979) *BioSystems*, vol. 11, pp. 1–7.
Masinovsky, Z. et al. (1989) *BioSystems*, vol. 22, pp. 305–310.
Martinez Luque-Romero, M. et al. (1986) *BioSystems*, vol. 19, pp. 267–272.
Matsuno, K. (1982) *BioSystems*, vol. 15, pp. 1–11.
Matsuno, K. (1984) *BioSystems*, vol. 17, pp. 11–14.
Matsuno, K. (1981) *BioSystems*, vol. 14, pp. 163–170.
McAlhaney, W.W. et al. (1976) *BioSystems*, vol. 8, pp. 45–50.
Melius, P. et al. (1987) *BioSystems*, vol. 20, pp. 213–217.

Melius, P. et al. (1975) *Bioorganic Chemistry*, vol. 4, pp. 385–391.

Melius, P. (1979) *BioSystems*, vol. 11, pp. 125–132.

Miquel, J. et al. (1971) *Currents in Modern Biology*, vol. 3, pp. 299–306.

Nakashima, T. et al. (1980) *J. Mol. Evol.*, vol. 15, pp. 161–168.

Nakashima, T. et al. (1981) *BioSystems*, vol. 14, pp. 151–161.

Novak, V.J.A. (1984) *Origins of Life*, vol. 14, pp. 513–522.

Olafsson, P.G. et al. (1971) *Polymer Letters*, vol. 9, pp. 521–528.

Phillips, R.D. et al. (1974) *Int. J. Peptide Protein Res.*, vol. 6, pp. 309–319.

Przybylski, A.T. et al. (1982) *Die Naturwissenschaften*, vol. 69, pp. 561–563.

Przybylski, A.T. et al. (1984) *Applied Biochemistry and Biotechnology*, vol. 10, pp. 301–307.

Przybylski, A.T. (1985) *BioSystems*, vol. 17, pp. 281–288.

Rohlfing, D.L. (1975) *Origins of Life*, vol. 6, pp. 203–209.

Rohlfing, D.L. (1970) *Science*, vol. 169, pp. 998–1000.

Rohlfing, D.L. (1967) *Archives of Biochemistry and Biophysics*, vol. 118, pp. 468–474.

Rohlfing, D.L. et al. *Catalytic Activities of Thermal Polyanhydro-α-Amino Acids*, pp. 373–418.

Rohlfing, D.L. et al. (1976) *BioSystems*, vol. 8, pp. 139–145.

Ryan, J.W. et al. (1973) *BioSystems*, vol. 5, pp. 115–118.

Saunders, M.A. et al. (1974) *BioSystems*, vol. 6, pp. 81–92.

Snyder, W.D. et al. (1975) *BioSystems*, vol. 7, pp. 222–229.

Sokol, P.K. (1974) *Journal of the American Oil Chemists' Society*, vol. 52, pp. 101–102.

Tschager et al. (1988) *Milchwirtschaftliche Berichte*, vol. 95, pp. 79–83.

Vaughan, G. et al. (1987) *BioSystems*, vol. 20, pp. 219–223.

Vol'kenshtein, M.V. (1989) *Molekulyarnaya Biologiya*, vol. 23(1), pp. 23–37.

Waelmeldt, T.V. et al. (1968) *Biochim. Biophys. Acta*, vol. 160, pp. 239–245.

Williams et al. (1991) *J. Biol. Chem.*, vol. 266, No. 8, pp. 5182–5190.

Yuki, A. et al. (1969) *Biochemical and Biophysical Research Communications*, vol. 36(4), pp. 657–663.

Zulaski et al. (1983) "New Carboxyalkyl Inhibitors of Brain Enkenphalinase", *J. Med. Chem.*, 26, pp. 60–65.

(1985) *Chemical Abstracts*, vol. No. 105(1), Abstract No. 12027p.

(1985) *Chemical Abstracts*, vol. No. 102(6), Abstract No. 50870d.

Chemical Abstract, vol. 80(9) Abst. No. 52392a (1974).

Bergeron, Raymond J., et al. (1994) "Macromolecular Self-Assembly of Diketopiperazine Tetrapeptides", *Journal of the American Chemical Society*, vol. 116, pp. 8479–8484.

Bergeron, Raymond J., et al. (1993) "A Comparative Study of the Iron-Clearing Properties of Desferrithiocin Analogues With Desferrioxamine B in a *Cebus* Monkey Model", *Blood*, vol. 81, No. 8, pp. 2166–2173.

Bergeron, Raymond J., et al. (1992) "A Comparison of the Iron–Clearing Properties of 1,2-Dimethyl-3-Hydroxypyrid-4-One, 1,2-Diethyl-3-Hydroxypyrid-4-One, and Deferoxamine", *Blood*, vol. 79, No. 7, pp. 1882–1890.

Bergeron, Raymond J., et al. (1991) "Evaluation of Desferrithiocin and Its Synthetic Analogs as Orally Effective Iron Chelators", *Journal of Medicinal Chemistry*, vol. 34, No. 7, pp. 2072–2078.

Bergeron, Raymond et al., "A Comparative Evaluation of Iron Clearance Models", *Annals New York Academy of Sciences*, pp. 378–393 (1990).

Andriuoli, G., et al. (1990), *Haemostasis* 20 (suppl. 1):154–158.

Caramazza, I., et al. (1991), *Thrombosis Research* 62:785–789.

Guarini, S., et al. (1983), *Experimentia* 41:350–352.

Guarini, S., et al. (1985), *Pharmacological Research Communications* 17(8):685–697.

Dal Pozzo, A., et al. (1989), *Thrombosis Research* 56:119–124.

Gelb, R., et al (1983), *Lite Sciences* 33(1):83–85.

Watterberg et al. (1988), *Pediatric Research*, vol. 23, No. 4, part 2, p. 570A, column 1, abstract No. 2209.

Bernstein (1985), *Chest* 87(1):68S–73S.

Damage et al. (1988), *Diabetes* 246–251.

184358, *Chemical Abstracts*:83 (1975).

Amino, Y., et al., *Chem. Pharm. Bull.* 36(11):4426–4434 (1988).

Baughman, R.A. et al., *Proc. of the 6th Inter'l. Symp. on Recent Advs. in Drug Delivery Systems, Ctr. for Controlled Chem. Delivery, University of Utah*, Feb. 22–25, 1993, Salt Lake City, UT, pp. 179–180 "Method for Assessing The Stability of Proteinoid Microspheres".

Haas, S. et al., "Assessment Of Stability Of Proteinold Microspheres", *Proceed. Intern. Symp. Control. Rel. Bioact. Mater.*, 20 (1993), Controlled Release Society, Inc.

X. Ma, et al., *Proceed. Intern. Syrup. Control. Rel Bioact. Mater.*, 20 (1993), Controlled Release Society, Inc. "IN VITRO Mechanistic Investigation of the Proteinold Microsphere Oral Delivery System".

Yen, H.–R H., et al., "Adsorption of Sulforhodamine 101 on Proteinold Microspheres" *Proceed. Intern. Symp. Control. Rel. Bioact. Mater.*, 20 (1993), Controlled Release Society, Inc.

Presented at "*IBC Rational Drug Design Conference*", San Diego, Calif.—Dec. 1994.

Bergeron, Raymond J. et al., *J. Am. Chem. Soc.* 1994, 116,8479–8484 "Macromolecular Self–Assembly of Diketopiperazine Tetrapeptides".

Leone–Bay et al., Presented at "Winter Conference on Medicinal and Bioorganic Chemistry" Steamboat Springs, Colorado—Feb. 1995 Microsphere Formation and Drug Delivery in a Series of Derivatized Amino Acids.

Santiago et al., *Pharm. Res.* 11: 1994, pp.8–298 "Oral Delivery of Heparin Microspheres made with Modified Amino Acids".

Leone–Bay et al., *Pharm. Res.* 11: 1994, p.S–121 "Oral Delivery of Heparin using Acylated Amino Acids".

Sarubbi et al., *Pharm. Res.* 1994, p.S–299 "Oral Calcitonin Delivery using the PODDS Technology".

Leipold et al., *Pharm. Res.* 11: 1994, p.S–298 "Oral Delivery of Interferon in Rats and Primates".

Santiago et al., *Pharm. Res.* 11: 1994, p.S–298 "Evaluation in Rats of Vehicles for the Oral Delivery of Low Molecular Weight Heparin".

Milstein et al., *Symposia Abstracts*. AAPS Annual Meeting, San Antonia, TX, Nov. 15–19, 1993.

X. Ma et al., PDD 7303 *Pharmaceutical Research* 9(10):S–244, 1992 (Oct. Supplement).

Santiago et al. "Initial Studies In The Assessment of Proteinold Microsphere Activity" *Proceed. Intern. Symp. Control. Rel. Bioact. Mater.*, 20 (1993), Controlled Release Society, Inc.

Santiago et al. "Proteinold Microspheres For The Oral Delivery of Heparin" *Proceed. Intern. Symp. Control. Rel. Bioact. Mater.*, 19 (1992), Controlled Release Society, Inc. pp. 514–515.

Santiago et al. "Oral Immunization of Rats with Influenza Virus M Protein (M1) Microspheres" *Proceed. Intern. Symp. Control. Rel. Bioact. Mater.*, 19 (1992), Controlled Release Society, Inc., p. 116–117.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater,* 19 (1992), Controlled Release Society, Inc. pp. 516–517.

Doris K. Chiappetta, *Eastern Analytical Symposium,* Nov. 17, 1992 "Solutions for Problems in Bioanalysis".

Elizabeth A. Harris. M.S., *Eastern Analytical Symposium,* Nov. 17, 1992 "Solutions for Problems in Bioanaylsis".

*AAPS 6th Ann. Meeting and Expo.,* "Proteinoids—A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium—Advances in Gene Technology: Protein Engineering and Beyond,* Jan. 17–22, 1993.

Xinghang Ma, et al. "Stability Study of Drug–loaded Proteinoid Microsphere Formulations during Freeze–drying" *Journal of Drug Targeting,* 1994, vol. 2, pp. 9–21.

Baughman et al., "Screening Candidate Microsphere Formulations By Incubating In Simulated Digestive Fluids" *Proc. of the 6th Intern'l. Sympo. on Recent Advances in Drug Delivery Systems,* Ctr. for Controlled Chem. Delivery, University of Utah, Feb. 22–25, 1993, pp. 181–182.

Robert O. Dillman, M.D., Annals of Internal Medicine 1989:111 pp. 592–600, "Monoclonal Antibodies for Treating Cancer".

Brendan D. Curti, Critical Reviews in Oncology/Hematology, 1993: 14 pp. 29–39 "Physical barriers to drug delivery in tumors".

V. Hird et al, Genes and Cancer, edited by Desmond Carney & Karol Sikora, pp. 183–189, "Immunotherapy with Monoclonal Antibodies". (1990).

Michael E. Osband et al., Immunology Today, vol. 11, No. 6 1990, pp. 93–95, "Problems in the investigational study and clinical use of cancer immunotherapy".

Tibtech Feb. 1993 vol. 11, pp. 42–44 "Therapeutic antibodies—the coming of age".

Thomas A. Waldmann, Articles Jun. 21, 1991, pp. 1657–1662, "Monoclonal Antibodies in Diagnosis and Therapy".

Douglas et al., *Chemistry and Industry,* 22:748–751, 1985.

Finch, *Chemistry and Industry,* 22:752–756, 1985.

SPRAY DRYING METHOD AND APPARATUS

FIELD OF THE INVENTION

The present invention relates to methods and apparatus for the production of microspheres which optionally contain an active agent and particularly a biologically active agent. These microspheres are of two basic forms, the matrix and the capsule. More particularly, the present invention relates to methodology and apparatus for producing proteinold, modified amino acid, or protein microspheres by spray drying techniques.

BACKGROUND OF THE INVENTION

Many present systems for delivering active agents to targets are severely limited by biological, chemical and physical barriers, which are imposed by the environment through which delivery occurs, the environment of the target of delivery, or the target itself. For example, oral delivery of many biologically active agents, such as, for example, insulin, would be the route of choice if not for chemical and physicochemical barriers such as extreme pH in the stomach, powerful digestive enzymes, and gastrointestinal membranes which are impermeable to the active agent.

Much research has been devoted to developing designs of and manufacturing methods for effective oral drug delivery. For example, Fulwyler, et al., U.S. Pat. No. 4,162,282, disclose the production of uniform particles by introducing a laminar stream of a core liquid into a flowing body of an immiscible sheath liquid. The liquids, either of which may contain dispersed materials, and are expelled from a nozzle to form a liquid jet which is disturbed at a uniform periodic rate to create droplets.

U.S. Pat. No. 4,422,985 to Morishita, et al. describes an encapsulation in which a triple jet is introduced into a flow of cooling liquid to form capsules. The triple jet includes an inner jet of a material to be encapsulated, a middle coaxial jet of a capsule forming material around the inner jet, and an outer coaxial jet of a heated liquid surrounding the middle jet.

U.S. Pat. No. 4,481,157 to Morishita, et al. describes a microcapsule production device which includes an inner pipe for extruding a material to be encapsulated and a coaxial outer pipe for extruding an encapsulating material. Both materials are introduced into a flow of a coagulating agent to produce microcapsules.

Microspheres formed from mixed amino acid proteinolds (non-naturally occurring (i.e., artificial) polymers of mixed amino acids) have been described as delivery vehicles for pharmaceuticals in U.S. Pat. No. 4,925,673 to Steiner et al. These microspheres are typically prepared by a batch-type thermal condensation.

Shioya, et al., U.S. Pat. No. 5,040,960, describe a method and an apparatus for the production of encapsulated bodies in which a core fluid is ejected from a double-walled cylindrical nozzle into a reaction tank containing a solution capable of forming gel skins around the core fluid. The double walled nozzle allows the introduction of air to control the size of the droplets of the core fluid introduced into the reaction tank.

Mazer, et al., U.S. Pat. No. 5,160,742, describe prolamine/ enteric coated microspheres which contain an active agent, while Mathiowitz, et al., U.S. Pat. No. 5,271,961, disclose pharmacologically active agents containing prolamine microspheres prepared by phase separation.

*Encapsulation News*, vol. 1, number 2, Southwest Research Institute, San Antonio, Tex. (1982), describes a method for producing encapsulated bodies using an air suspension coater. The batch-type air suspension coater utilizes a fluid bed of salt which is repeatedly cycled past a spray nozzle. The spray nozzle applies a wax coating around a cargo. Microcapsules are also prepared using a rotating centrifugal extrusion nozzle. The rotating nozzle apparatus has an inner nozzle for delivering the material to be encapsulated and an outer nozzle for delivering the shell material. The shell material is pumped through an annular space between the inner and outer nozzles and coats the material to be encapsulated following ejection from the rotating nozzle apparatus.

The manufacture of proteinold, modified amino acid, or protein microspheres presents significant challenges. These carrier materials are conventionally initially solubilized before microsphere formation. However, the solubilities of these carrier materials vary dependent upon the amino acid content of the carrier and consequent functional groups on their surfaces. These carriers also present other processing problems. Many proteinold, modified amino acid, or protein carriers are unstable, water insoluble, or soluble primarily only in volatile organic solvents. Volatile organic solvents are generally flammable, expensive, environmentally unfriendly, and consequently, commercially impractical to use.

Thus, there is a need for rapid and inexpensive methods to prepare microsphere delivery systems. It has now been discovered that microsphere delivery systems incorporating proteinolds, modified amino acids, proteins or conventional enteric coating materials can be prepared rapidly and economically by modified spray drying techniques.

Therefore, an object of the present invention is to provide methods for producing stable microspheres, and preferably microcapsules, for the delivery of active agents and particularly for the oral delivery of biologically active agents. Another object of the present invention is to provide an apparatus for economically producing these microspheres by spray drying.

SUMMARY OF THE INVENTION

The present invention provides a method for preparing microspheres which optionally contain an active agent. The method comprises:

(A) nebulizing each of
   (a) a carrier vehicle comprising a microsphere forming carrier, and
   (b) a precipitator;
      wherein the carrier vehicle (a) or the precipitator (b) optionally includes an active agent; and
(B) contacting said carrier vehicle and said precipitator. Preferably, the nebulizing and contacting are preferred simultaneously. In a preferred embodiment, the carrier is selected from the group consisting of
   (i) a proteinoid;
   (ii) an acylated amino acid or a salt thereof;
   (iii) an acylated polyamino acid or a salt thereof;
   (iv) a sulfonated amino acid or a salt thereof;
   (v) a sulfonated polyamino acid or a salt thereof;
   (vi) a protein or salt thereof;
   (vii) an enteric coating; or
   (viii) any combination thereof.

If an active agent is present, the microsphere will include the active agent.

In an alternate embodiment, the method comprises:

(a) nebulizing an aqueous acid/carrier solution comprising:
  (i) volatile acid;
  (ii) a microsphere forming carrier; and
  (iii) optionally an active agent;

wherein the volume:volume ratio of acid to water in the carrier solution is at least about 3:7, and (b) decreasing the ratio to less than about 3:7, to yield the microspheres. In a preferred embodiment, the carrier is selected from the group consisting of
- (i) a proteinoid,
- (ii) an acylated amino acid or a salt thereof;
- (iii) an acylated polyamino acid or a salt thereof;
- (iv) a sulfonated amino acid or a salt thereof;
- (v) a sulfonated polyamino acid or a salt thereof;
- (vi) a protein or a salt thereof;
- (vii) an enteric coating material;
- (viii) any combination thereof.

Another aspect of the present invention provides a spray drying apparatus for producing these microspheres. The apparatus comprises:

(A) a spray nozzle comprising:

(i) a first delivery pipe having an inlet portion and an outlet portion, the first pipe outlet portion in open communication with a nozzle outlet;

(ii) a second delivery pipe having an inlet and an outlet portion, the second pipe outlet portion in open communication with the nozzle outlet; and (iii) a pressurized gas delivery jacket having an inlet portion and an outlet portion, the jacket outlet portion surrounding the first and second pipe outlet portions but not the nozzle outlet, and in open communication with the nozzle outlet; as well as (B) a carrier vehicle reservoir in communication with the first delivery pipe;

(C) a precipitator reservoir in communication with the second delivery pipe;

(D) a pressurized gas supply in communication with the gas delivery jacket;

(E) a dryer source; and (F) a collection reservoir.

BRIEF DESCRIPTION OF THE DRAWINGS

FIG. 1A is an illustration of a hollow matrix microsphere with a cargo.

FIG. 1B is an illustration of a solid matrix microsphere with a cargo.

FIG. 1C is an illustration of a microcapsule microsphere with a cargo.

FIG. 1D is an illustration of an alternate microcapsule microsphere with a cargo.

FIG. 2 is a schematic illustration of a spray drying apparatus of the present invention.

FIG. 3 is a sectional view of a spray drying nozzle of the present invention.

DETAILED DESCRIPTION OF THE INVENTION

Microspheres are useful in the delivery of active agents because they protect any active agent cargo until it is delivered to a target. Microspheres are particularly useful in the oral delivery of biologically active agents such as, for example, pharmaceutically active agents.

Microspheres containing an active agent can be generally of the matrix form or the capsule form. The hollow matrix spheroid form is illustrated in FIG. 1A. The center of the sphere is hollow and the cargo or active agent (1) is distributed throughout a carrier matrix (3). The solid matrix form is illustrated in FIG. 1B. The carrier matrix (3) forms a continuum in which the cargo (1) is distributed. The microcapsule form is illustrated in FIGS. 1C and 1D. The encapsulated material or cargo (1) can be either in solution as illustrated in FIG. 1C, or a solid (1) as illustrated in FIG. 1D with the carrier (3) forming a shell around the cargo.

The methods of the present invention are cost-effective for preparing microspheres which may contain active agents, are simple to perform, and are amenable to industrial scale-up for commercial production.

Carriers

Carriers suitable for use in the present invention are microsphere forming carriers. These carriers include, without limitation, proteinolds, acylated amino acids or poly amino acids or salts thereof, sulfonated amino acids or poly amino acids or salts thereof, proteins or salts thereof, enteric coating materials, or any combination thereof.

Amino acids are the basic materials used to prepare many of the carriers useful in the present invention. Amino acids are any carboxylic acids having at least one free amino group and include naturally occurring and synthetic amino acids. The preferred amino acids for use in the present invention are α-amino acids and, most preferably, are naturally occurring α-amino acids. Many amino acids and amino acid esters are readily available from a number of commercial sources such as Aldrich Chemical Co. (Milwaukee, Wis., U.S.A.); Sigma Chemical Co. (St. Louis, Mo., U.S.A.); and Fluka Chemical Corp. (Ronkonkoma, N.Y., U.S.A.).

Representative, but not limiting, amino acids suitable for use in the present invention are generally of the formula $$H—N(R^1)—(R^2—\overset{\overset{\large O}{\|}}{C})—OH \qquad I$$

wherein:

$R^1$ is hydrogen, $C_1$–$C_4$ alkyl, or $C_2$–$C_4$ alkenyl, $C_2$–$C_4$;

$R^2$ is $C_1$–$C_{24}$ alkyl, $C_2$–$C_{24}$ alkenyl, $C_2$–$C_{24}$ alkylidene, $C_3$–$C_{10}$ cycloalkyl, $C_3$–$C_{24}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl), or naphthyl ($C_2$–$C_{10}$ alkenyl);

$R^2$ being optionally substituted with $C_1$–$C_4$ alkyl, $C_2$–$C_4$ alkenyl, $C_1$–$C_4$ alkoxy, —OH, —SH, $—CO_2R^3$, $C_3$–$C_{10}$ cycloalkyl, $C_3$–$C_{10}$ cycloalkenyl, heterocycle having 3–10 ring atoms wherein the hetero atom is one or more of N, O, S, or any combination thereof, aryl, ($C_1$–$C_{10}$ alk)aryl, ar($C_1$–$C_{10}$ alkyl) or any combination thereof;

$R^2$ being optionally interrupted by oxygen, nitrogen, sulfur, or any combination thereof; and $R^3$ is hydrogen, $C_1$–$C_4$ alkyl, or $C_2$–$C_4$ alkenyl.

The preferred naturally occurring amino acids for use in the present invention as amino acids or components of a peptide are alanine, arginine, asparagine, aspartic acid, citrulline, cysteine, cystine, glutamic acid, glutamine, glycine, histidine, isoleucine, leucine, lysine, methionine, ornithine, phenylalanine, proline, serine, threonine, tryptophan, tyrosine, valine, hydroxyproline, β-carboxyaspartic acid, γ-carboxyglutamic acid, phenylglycine, or O-phosphoserine. The most preferred amino acids are arginine, aspartic acid, glutamic acid, leucine, lysine, phenylalanine, tyrosine, tryptophan, valine, and phenylglycine.

The preferred non-naturally occurring amino acids for use in the present invention are β-alanine, α-amino butyric acid, γ-amino butyric acid, γ-(aminophenyl) butyric acid, α-amino isobutyric acid, ε-amino caproic acid, 7-amino heptanoic acid, β-aspartic acid, aminobenzoic acid, aminophenyl acetic acid, aminophenyl butyric acid, γ-glutamic acid, cysteine (ACM), ε-lysine, methionine sulfone, norleucine, norvaline, ornithine, d-ornithine, p-nitrophenylalanine, hydroxy proline, 1,2,3,4,-tetrahydroisoquinoline-3-carboxylic acid, and thioproline.

Poly amino acids are either peptides or two or more amino acids linked by a bond formed by other groups which can be linked, e.g., an ester or an anhydride linkage. Special mention is made of non-naturally occurring poly amino acids and particularly non-naturally occurring hetero-poly amino acids, i.e. of mixed amino acids.

Peptides are two or more amino acids joined by a peptide bond. Peptides can vary in length from di-peptides with two amino acids to polypeptides with several hundred amino acids. See, Walker, *Chambers Biological Dictionary*, Cambridge, England: Chambers Cambridge, 1989, page 215. Special mention is made of non-naturally occurring peptides and particularly non-naturally occurring peptides of mixed amino acids. Special mention is also made of di-peptides tri-peptides, tetra-peptides, and penta-peptides, and particularly, the preferred peptides are di-peptides and tri-peptides. Peptides can be homo- or hetero-peptides and can include natural amino acids, synthetic amino acids, or any combination thereof.

Proteinolds

Proteinoids are artificial polymers of amino acids. Proteinoids preferably are prepared from mixtures of amino acids. Preferred proteinoids are condensation polymers, and most preferably, are thermal condensation polymers. These polymers may be directed or random polymers. Proteinoids can be linear, branched, or cyclical, and certain proteinoids can be units of other linear, branched, or cyclical proteinoids.

Special mention is made of diketopiperazines. Diketopiperazines are six member ring compounds. The ring includes two nitrogen atoms and is substituted at two carbons with two oxygen atoms. Preferably, the carbonyl groups are at the 2 and 5 ring positions. These rings can be optionally, and most often are, further substituted.

Diketopiperazine ring systems may be generated during thermal polymerization or condensation of amino acids or amino acid derivatives. (Gyore, J; Ecet M. *Proceedings Fourth ICTA (Thermal Analysis)*, 1974, 2, 387–394 (1974)). These six membered ring systems were presumably generated by intra-molecular cyclization of the dimer prior to further chain growth or directly from a linear peptide (Reddy, A. V., *Int. J. Peptide Protein Res.*, 40, 472–476 (1992); Mazurov, A. A. et al., *Int. J. Peptide Protein Res.*, 42, 14–19 (1993)).

Diketopiperazines can also be formed by cyclodimerization of amino acid ester derivatives as described by Katchalski et al., *J. Amer. Chem. Soc.*, 68, 879–880 (1946), by cyclization of dipeptide ester derivatives, or by thermal dehydration of amino acid derivatives and high boiling solvents as described by Kopple et al., *J. Org. Chem.*, 33 (2), 862–864 (1968).

Diketopiperazines typically are formed from α-amino acids. Preferably, the α-amino acids of which the diketopiperazines are derived are glutamic acid, aspartic acid, tyrosine, phenylalanine, and optical isomers of any of the foregoing.

Special mention is made of diketopiperazines of the formula

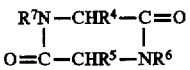     II wherein $R^4$, $R^5$, $R^6$, and $R^7$ independently are hydrogen, $C_1$–$C_{24}$ alkyl, $C_1$–$C_{24}$ alkenyl, phenyl, naphthyl, ($C_1$–$C_{10}$ alkyl)phenyl, ($C_1$–$C_{10}$ alkenyl)phenyl, ($C_1$–$C_{10}$ alkyl)naphthyl, ($C_1$–$C_{10}$ alkenyl)naphthyl ($C_1$–$C_{10}$ alkenyl); any of $R^4$, $R^5$, $R^6$, and $R^7$ independently may optionally be substituted with $C_1$–$C_4$ alkyl, $C_1$–$C_4$ alkenyl, $C_1$–$C_4$ alkoxy, —OH, —SH, and —$CO_2R^8$ or any combination thereof; $R^8$ is hydrogen, $C_1$–$C_4$ alkyl, or $C_1$–$C_4$ alkenyl; and any of $R^4$, $R^5$, $R^6$, and $R^7$ independently may optionally be interrupted by oxygen, nitrogen, sulfur, or any combination thereof.

The phenyl or naphthyl groups may optionally be substituted. Suitable, but non-limiting, examples of substituents are $C_1$–$C_6$ alkyl, $C_1$–$C_6$ alkenyl, $C_1$–$C_6$ alkoxy, —OH, —SH, or $CO_2R_9$ wherein $R^9$ is hydrogen, $C_1$–$C_6$ alkyl, or $C_1$–$C_6$ alkenyl.

Preferably, $R^6$ and $R^7$ independently are hydrogen, $C_1$–$C_4$ alkyl or $C_1$–$C_4$ alkenyl. Special mention is made of diketopiperazines which include the unsubstituted diketopiperazine in which $R^4$, $R^5$, $R^6$, and $R^7$ are hydrogen, and diketopiperazines which are substituted at one or both of the nitrogen atoms in the ring, i.e. mono- or di-N-substituted. Special mention is made of the N-substituted diketopiperazine wherein one or both of the nitrogen atoms is substituted with a methyl group.

Special mention is also made of diketopiperazines of the formula

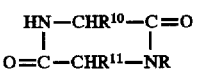     III wherein $R^{10}$ and $R^{11}$ independently are hydrogen, $C_1$–$C_{24}$ alkyl, $C_1$–$C_{24}$ alkenyl, phenyl, naphthyl, ($C_1$–$C_{10}$ alkyl) phenyl, ($C_1$–$C_{10}$ alkenyl) phenyl, ($C_1$–$C_{10}$ alkyl)naphthyl, ($C_1$–$C_{10}$ alkenyl) naphthyl, phenyl ($C_1$–$C_{10}$ alkyl), phenyl ($C_1$–$C_{10}$ alkenyl), naphthyl, ($C_1$–$C_{10}$ alkyl), and naphthyl ($C_1$–$C_{10}$ alkenyl); but both $R^{10}$ and $R^{11}$ can not be hydrogen; either or both $R^{10}$ and $R^{11}$ independently may optionally be substituted with $C_1$–$C_4$ alkyl, $C_1$–$C_4$ alkenyl, $C_1$–$C_4$ alkoxy, —OH, —SH, and —$CO_2R^{12}$ or any combination thereof; $R^{12}$ is hydrogen, $C_1$–$C_4$ alkyl, or $C_1$–$C_4$ alkenyl; and either or both $R^{10}$ and $R^{11}$ independently may optionally be interrupted by oxygen, nitrogen, sulfur, or any combination thereof.

The phenyl or naphthyl groups may optionally be substituted. Suitable, but non-limiting examples of substituents are $C_1$–$C_6$ alkyl, $C_1$–$C_6$ alkenyl, $C_1$–$C_6$ alkoxy, —OH, —SH, or $CO_2R^{13}$ wherein $R^{13}$ is hydrogen, $C_1$–$C_6$ alkyl or $C_1$–$C_6$ alkenyl. When one of $R^{10}$ and $R^{11}$ is hydrogen, the diketopiperazine is mono-carbon-(C)-substituted. When neither $R^{10}$ nor $R^{11}$ is hydrogen, the diketopiperazine is di-carbon-(C)-substituted.

Preferably, $R^{10}$, $R^{11}$, or both $R^{10}$ and $R^{11}$ contain at least one functional group, a functional group being a non-hydrocarbon portion responsible for characteristic reactions of the molecule. Simple functional groups are heteroatoms including, but not limited to halogens, oxygen, sulfur, nitrogen, and the like, attached to the carbon of an alkyl group by a single or multiple bond. Other functional groups include, but are not limited to, for example, hydroxyl groups, carboxyl groups, amide groups, amine groups, substituted amine groups, and the like.

Preferred diketopiperazines are those which are substituted at one or two of the carbons of the ring with a functional group that includes at least one carboxyl functionality.

Modified Amino Acids and Poly Amino Acids

Modified amino acids, poly amino acids, or peptides are either acylated or sulfonated and include amino acid amides and sulfonamides.

Acylated Amino Acids and Poly Amino Acids

Although any acylated amino acids or poly amino acids are useful in the present invention, special mention is made of acylated amino acids having the formula

    IV wherein Ar is a substituted or unsubstituted phenyl or naphthyl;

Y is

$R^{14}$ has the formula $-N(R^{16})-R^{15}$

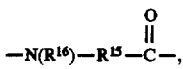

wherein:

$R^{15}$ is $C_1$ to $C_{24}$ alkyl, $C_1$ to $C_{24}$ alkenyl, phenyl, naphthyl, ($C_1$ to $C_{10}$ alkyl) phenyl, ($C_1$ to $C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);

$R^{15}$ is optionally substituted with $C_1$ to $C_4$ alkyl, $C_1$ to $C_4$ alkenyl, $C_1$ to $C_4$ alkoxy, —OH, —SH and —$CO_2R^{17}$, cycloalkyl, cycloalkenyl, heterocyclic alkyl, alkaryl, heteroaryl, heteroalkaryl, or any combination thereof;

$R^{17}$ is hydrogen, $C_1$ to $C_4$ alkyl or $C_1$ to $C_4$ alkenyl;

$R^{15}$ is optionally interrupted by oxygen, nitrogen, sulfur or any combination thereof; and $R^{16}$ is hydrogen, $C_1$ to $C_4$ alkyl or $C_1$ to $C_4$ alkenyl.

Special mention is also made of those having the formula

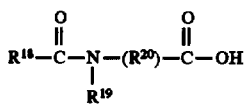    V wherein:

$R^{18}$ is (i) $C_3$–$C_{10}$ cycloalkyl, optionally substituted with $C_1$–$C_7$ alkyl, $C_2$–$C_7$ alkenyl, $C_1$–$C_7$ alkoxy, hydroxy, phenyl, phenoxy or —$CO_2R^{21}$, wherein $R^1$ is hydrogen, $C_1$–$C_4$ alkyl, or $C_2$–$C_4$ alkenyl; or (ii) $C_1$–$C_6$ alkyl substituted with $C_3$–$C_{10}$ cycloalkyl;

$R^{19}$ is hydrogen, $C_1$–$C_4$ alkyl, or $C_2$–$C_4$ alkenyl;

$R^{20}$ is $C_1$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_1$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl) or naphthyl ($C_2$–$C_{10}$ alkenyl);

$R^{20}$ being optionally substituted with $C_1$–$C_4$ alkyl, $C_2$–$C_4$ alkenyl, $C_1$–$C_4$ alkoxy, —OH, —SH, —$CO_2R^{22}$, $C_3$–$C_{10}$ cycloalkyl, $C_3$–$C_{10}$ cycloalkenyl, heterocycle having 3–10 ring atoms wherein the hetero atom is one or more of N, O, S or any combination thereof, aryl, ($C_1$–$C_{10}$ alk)aryl, ar($C_1$–$C_{10}$ alkyl), or any combination thereof;

$R^{20}$ being optionally interrupted by oxygen, nitrogen, sulfur, or any combination thereof; and $R^{22}$ is hydrogen, $C_1$–$C_4$ alkyl, or $C_2$–$C_4$ alkenyl.

Some preferred acylated amino acids include salicyloyl phenylalanine, and the compounds having the formulas:

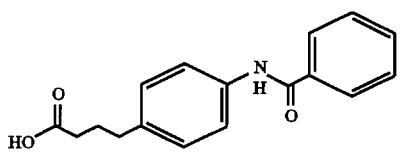    VI

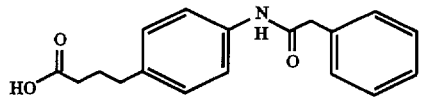    VII

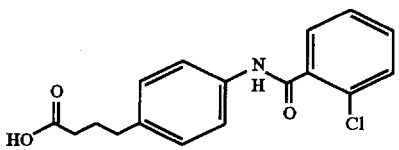    VIII

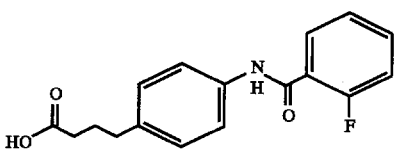    IX

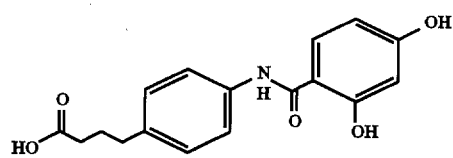    X

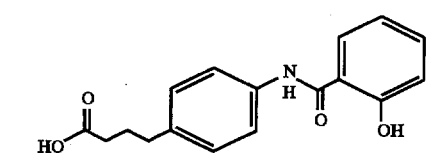    XI

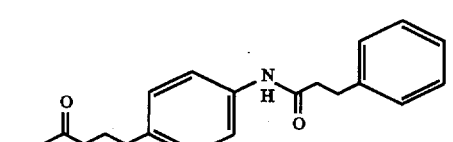    XII

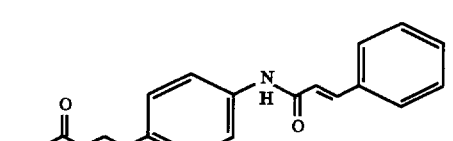    XIII

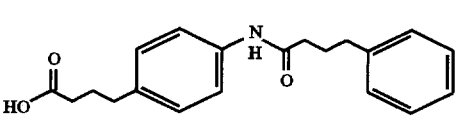    XIV

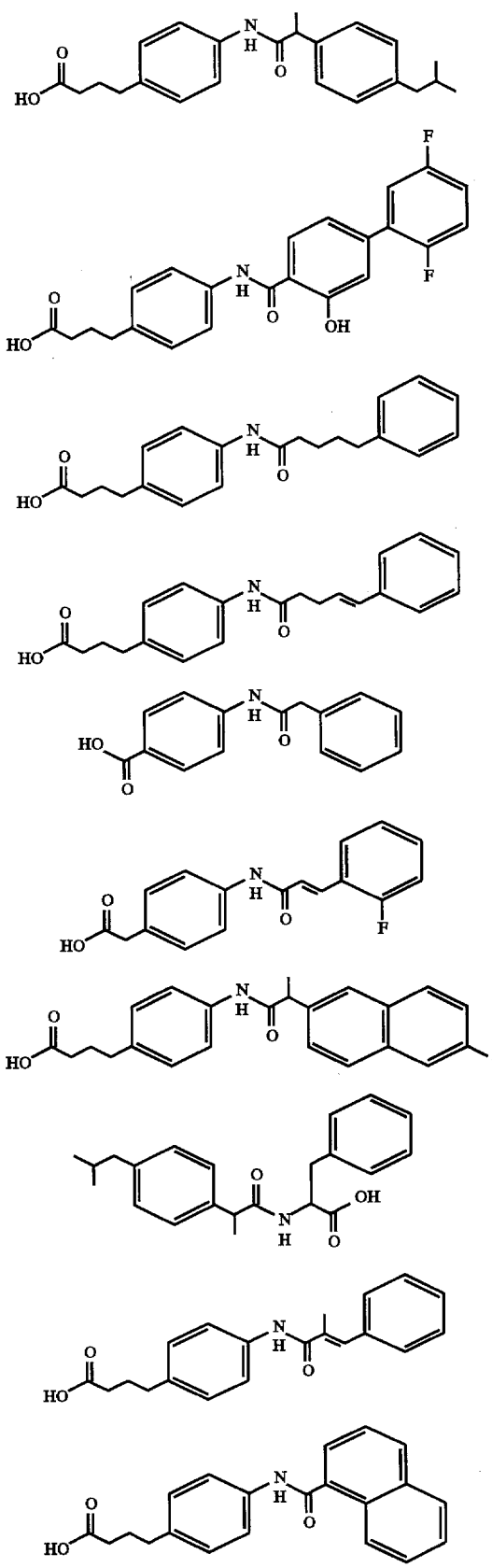
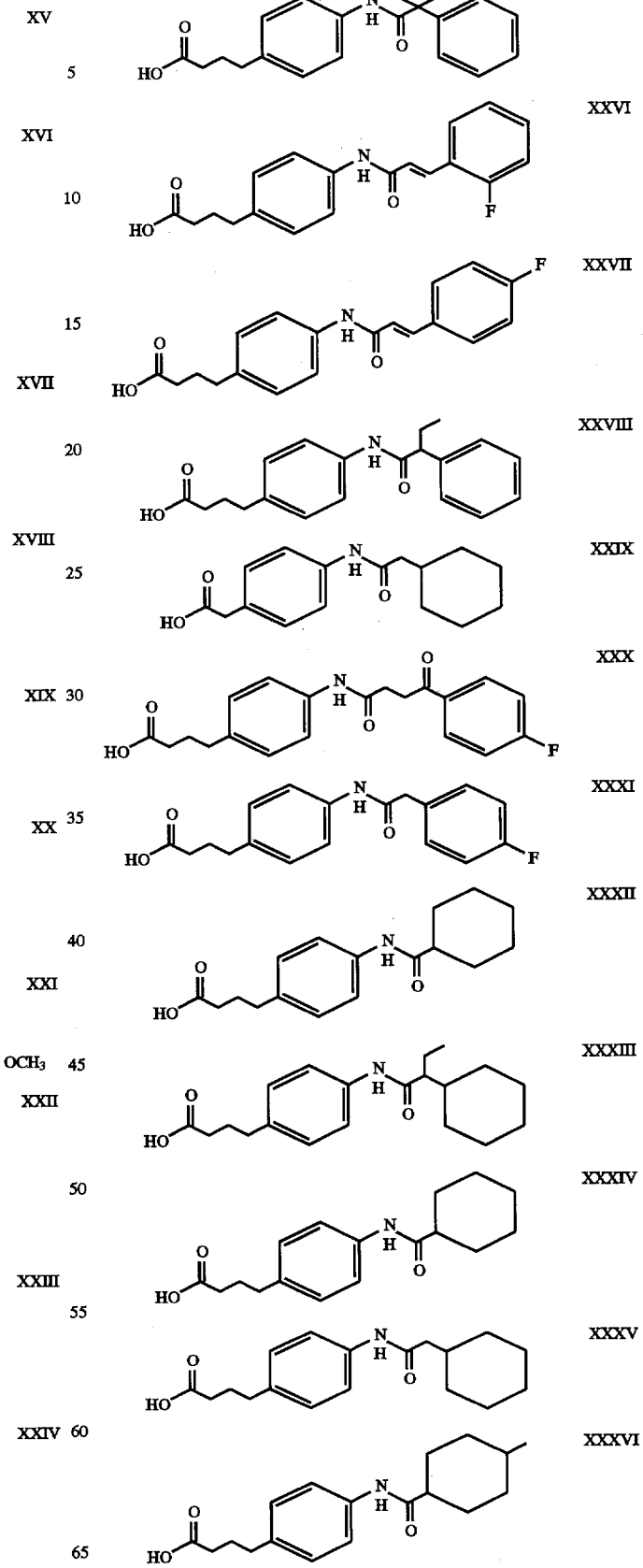

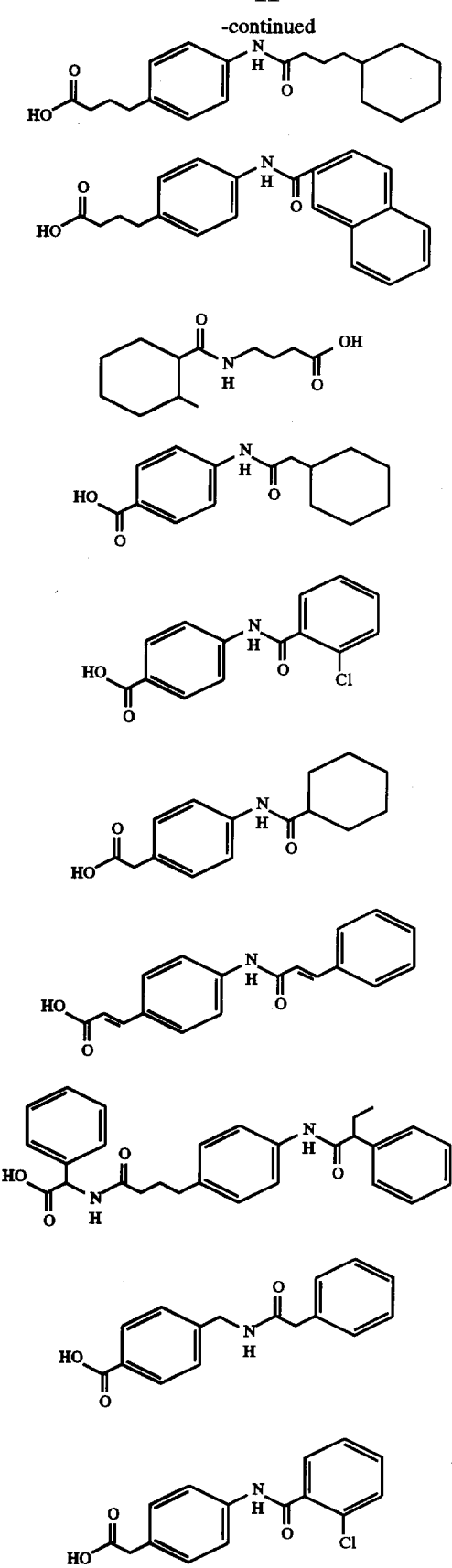

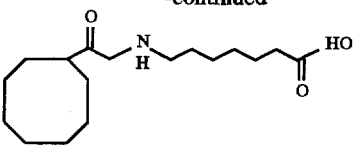
XLVII

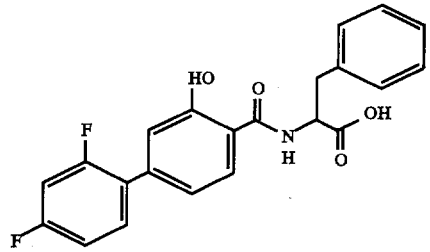
XLVIII

Special mention is made of compounds having the formula

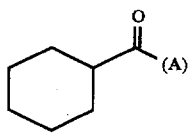
XLIX wherein A is Tyr, Leu, Arg, Trp, or Cit; and optionally wherein if A is Tyr, Arg, Trp or Cit; A is acylated at 2 or more functional groups.

Preferred compounds are those wherein A is Tyr; A is Tyr and is acylated at 2 functional groups; A is Leu; A is Arg; A is Arg and is acylated at 2 functional groups; A is Trp; A is trp and is acylated at 2 functional groups; A is Cit; and A is Cit and is acylated at 2 functional groups.

Special mention is also made of compounds having the formula:

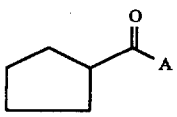
L wherein A is Arg or Leu; and wherein if A is Arg, A is optionally acylated at 2 or more functional groups;

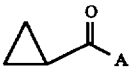
LI where A is leu or phenylglycine;

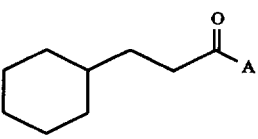
LII wherein A is phenylglycine; and

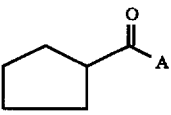
LIII wherein A is phenylglycine.

Acylated amino acids may be prepared by reacting single amino acids, mixtures of two or more amino acids, or amino acid esters with an amine modifying agent which reacts with free amino moieties present in the amino acids to form amides.

Suitable, but non-limiting, examples of acylating agents useful in preparing acylated amino acids include acid chloride acylating agents having the formula

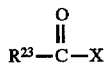

wherein:
$R^{23}$ an appropriate group for the modified amino acid being prepared, such as, but not limited to, alkyl, alkenyl, cycloalkyl, or aromatic, and particularly methyl, ethyl, cyclohexyl, cyclophenyl, phenyl, or benzyl, and X is a leaving group. Typical leaving groups include, but are not limited to, halogens such as chlorine, bromine, and iodine.

Examples of the acylating agents include, but are not limited to, acyl halides including, but not limited to, acetyl chloride, propyl chloride, cyclohexanoyl chloride, cyclopentanoyl chloride, cycloheptanoyl chloride, benzoyl chloride, hippuryl chloride and the like; and anhydrides, such as acetic anhydride, propyl anhydride, cyclohexanoic anhydride, benzoic anhydride, hippuric anhydride and the like. Preferred acylating agents include benzoyl chloride, hippuryl chloride, acetyl chloride, cyclohexanoyl chloride, cyclopentanoyl chloride, and cycloheptanoyl chloride.

The amine groups can also be modified by the reaction of a carboxylic acid with coupling agents such as the carbodiimide derivatives of amino acids, particularly hydrophilic amino acids such as phenylalanine, tryptophan, and tyrosine. An example includes dicyclohexylcarbodiimide and the like.

If the amino acid is multifunctional, i.e. has more than one —OH, —$NH_2$ or —SH group, then it may optionally be acylated at one or more functional groups to form, for example, an ester, amide, or thioester linkage.

For example, in the preparation of many acylated amino acids, the amino acid is dissolved in an aqueous alkaline solution of a metal hydroxide, e.g., sodium or potassium hydroxide and the acylating agent added. The reaction time can range from about 1 hour and about 4 hours, preferably about 2–2.5 hours. The mixture is maintained at a temperature generally ranging between about 5° C. and about 70° C., preferably between about 10° C. and about 50° C. The amount of alkali employed per equivalent of $NH_2$ groups in the amino acids generally ranges between 1.25 moles and about 3 moles, and is preferably between about 1.5 moles and about 2.25 moles per equivalent of $NH_2$. The pH of the reaction solution generally ranges between about pH 8 and about pH 13, and is preferably between about pH 10 and about pH 12. The amount of amino modifying agent employed in relation to the quantity of amino acids is based on the moles of total free $NH_2$ in the amino acids. In general, the amino modifying agent is employed in an amount ranging between 0.9 and about 2.5 mole equivalents, preferably between about 1.00 and about 1.25 equivalents, per molar equivalent of total $NH_2$ groups in the amino acids.

The modified amino acid formation reaction is quenched by adjusting the pH of the mixture with a suitable acid, e.g., concentrated hydrochloric acid, until the pH reaches between about 2 and about 3. The mixture forms a precipitate and the modified amino acids are collected by filtration or decantation. The filtrate is discarded. The crude modified amino acids are then mixed with water, and pH is adjusted to about 6 to about 8 with a suitable base. Insoluble materials are removed by filtration, and the filtrate is dried in vacuo.

The yield of modified amino acids generally ranges between about 30 and about 60%, and usually about 45%. The present invention also contemplates amino acids which have been modified by multiple acylation, e.g., diacylation or triacylation.

If amino acid esters or amides are the starting materials, they are dissolved in a suitable organic solvent such as dimethylformamide or pyridine and are reacted with the amino modifying agent at a temperature ranging between about 5° C. and about 70° C., preferably about 25° C., for a period ranging between about 7 and about 24 hours. The amount of amino modifying agents used relative to the amino acid esters are the same as described above for amino acids.

Thereafter, the reaction solvent is removed under negative pressure and optionally the ester or amide functionally can be removed by hydrolyzing the modified amino acid ester with a suitable alkaline solution, e.g., 1N sodium hydroxide, at a temperature ranging between about 50° C. and about 80° C., preferably about 70° C., for a period of time sufficient to hydrolyze off the ester group and form the modified amino acid having a free carboxyl group. The hydrolysis mixture is then cooled to room temperature and acidified, e.g., with an aqueous hydrochloric acid solution, to a pH ranging between about 2 and about 2.5. The modified amino acid precipitates out of solution and is recovered by conventional means such as filtration or decantation.

The modified amino acids may be purified by acid precipitation, recrystallization, or by fractionation on solid column supports. Fractionation may be performed on a suitable solid column supports such as silica gel, alumina, using solvent mixtures such as acetic acid/butanol/water as the mobile phase; reverse phase column supports using trifluoroacetic acid/acetonitrile mixtures as the mobile phase; and ion exchange chromatography using water as the mobile phase. The modified amino acids may also be purified by extraction with a lower alcohol such as methanol, butanol, or isopropanol to remove impurities such as organic salts.

The modified amino acids generally are soluble in neutral or alkaline aqueous solution (pH≧9.0); partially soluble in ethanol, n-butanol and 1:1 (v/v) toluene/ethanol solution; and insoluble in water. The alkali metal salts, e.g., the sodium salt of the derivatized amino acids are generally soluble in water at about a pH of 6–8.

In acylated poly amino acids, one or more of the amino acids may be modified (acylated). Modified poly amino acids may include one or more acylated amino acid(s). Although linear modified poly amino acids will generally include only one acylated amino acid, other poly amino acid configurations can include more than one acylated amino acid. Poly amino acids can be polymerized with the acylated amino acid(s) or can be acylated after polymerization.

Special mention is made of the compound:

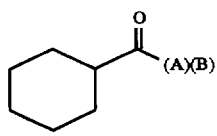

LIV wherein A and B independently are Arg or Leu.

Sulfonated Amino Acids and Poly Amino Acids

Sulfonated amino acids and poly amino acids are modified by sulfonating at least one free amine group with a sulfonating agent which reacts with at least one of the free amine groups present.

Special mention is made of compounds of the formula $$Ar-y-(R^{24})_n-OH \qquad LV$$

wherein Ar is a substituted or unsubstituted phenyl or naphthyl;
Y is $-SO_2-$, $R^{24}$ has the formula

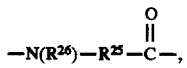

wherein:

$R^{25}$ is $C_1$ to $C_{24}$ alkyl, $C_2$ to $C_{24}$ alkenyl, $C_2$ to $C_{20}$ alkylidene, phenyl, naphthyl, ($C_1$ to $C_{10}$ alkyl) phenyl, ($C_1$ to $C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);

$R^{25}$ is optionally substituted with $C_1$ to $C_4$ alkyl, $C_1$ to $C_4$ alkenyl, $C_1$ to $C_4$ alkoxy, $-OH$, $-SH$ and $-CO_2R^{27}$ or any combination thereof;

$R^{27}$ is hydrogen, $C_1$ to $C_4$ alkyl or $C_1$ to $C_4$ alkenyl;

$R^{25}$ is optionally interrupted by oxygen, nitrogen, sulfur or any combination thereof; and $R^{26}$ is hydrogen, $C_1$ to $C_4$ alkyl or $C_1$ to $C_4$ alkenyl.

Suitable, but non-limiting, examples of sulfonating agents useful in preparing sulfonated amino acids include sulfonating agents having the formula $R^{28}-SO_2-X$ wherein $R^{28}$ is an appropriate group for the modified amino acid being prepared such as, but not limited to, alkyl, alkenyl, cycloalkyl, or aromatics and X is a leaving group as described above. One example of a sulfonating agent is benzene sulfonyl chloride.

Modified poly amino acids and peptides may include one or more sulfonated amino acid(s). Although linear modified poly amino acids and peptides used generally include only one sulfonated amino acid, other poly amino acid and peptide configurations can include more than one sulfonated amino acid. Poly amino acids and peptides can be polymerized with the sulfonated amino acid(s) or can be sulfonated after polymerization.

Proteins

Proteins are naturally occurring (i.e. not artificial) polymers of amino acids.

Enteric Coating Materials

Enteric coating materials known to those skilled in the art such as, for example, cellulose acetate trimellitate (CAT) and cellulose acetate phthalate (CAP), are suitable for use in the preservation as well.

Solvents

The carriers are typically provided in a vehicle such as a solution or a slurry. Appropriate solvents for these solutions or slurries typically include, but are not limited to, water or mildly acidic solvents. The solution form of the carrier vehicle is preferred.

However, it has been found that many carriers, and particularly proteinoids, acylated amino acids or poly amino acids, sulfonated amino acids or poly amino acids, and proteins, that are insoluble or relatively insoluble in neutral or mildly active solutions are soluble in aqueous organic acidic solutions wherein the volume to volume ratio of acid to water is greater than about 3:7. Suitable aqueous acid solvents in this embodiment of the present invention are volatile acids, such as for example, aqueous acetic acid, aqueous formic acid, and the like. These acids will volatilize upon nebulization or can be diluted in the aqueous solution, thereby decreasing the concentration of the acid and reversing the solubility of the carrier even in the absence of a precipitator.

Precipitators

The precipitator may be any compound or solution which will cause the carrier material to precipitate out of the carrier vehicle and form microspheres containing the active agent. The precipitator is preferably provided in the form of a solution. While many precipitator solutions are contemplated, acidic solutions are generally preferred for use with neutral carrier solutions. Examples of precipitators include, but are not limited to, water, dilute acetic acid (less than 10%), dilute formic acid (less than 10%), and citric acid. However, the choice of precipitators is generally predicated on the choice of carrier as explained below. The precipitator should not adversely affect the active agent in that, in the presence of the precipitator, the active agent should either retain its activity or only reversibly change activity.

Active Agents

Active agents suitable for use in the present invention include any active agents that may be incorporated into a microsphere. These agents include, for example, biologically active agents and chemically active agents, including, but not limited to, fragrances, as well as other active agents such as, for example, cosmetics.

Biologically active agents include, but are not limited to, pesticides, pharmacological agents, and therapeutic agents. For example, biologically active agents suitable for use in the present invention include, but are not limited to, peptides, and particularly small peptides; hormones, and particularly hormones which by themselves do not or only pass slowly through the gastro-intestinal mucosa and/or are susceptible to chemical cleavage by acids and enzymes in the gastro-intestinal tract; polysaccharides, and particularly mixtures of mucopolysaccharides; carbohydrates; lipids; or any combination thereof. Further examples include, but are not limited to, human growth hormones; bovine growth hormones; growth releasing hormones; interferons; interleukin-1;insulin; heparin, and particularly low molecular weight heparin; calcitonin; erythropoietin; atrial naturetic factor; antigens; monoclonal antibodies; somatostatin; adrenocorticotropin, gonadotropin releasing hormone; oxytocin; vasopressin; cromolyn sodium (sodium or disodium chromoglycate); vancomycin; desferrioxamine (DFO); antimicrobials, including, but not limited to anti-fungal agents, such as for example, itraconizol; or any combination thereof.

Microsphere Formation

Microsphere formation occurs when the precipitator and carrier vehicle are nebulized and contacted. The two can be nebulized separately and then contacted or can be nebulized and contacted together. Nebulization and contacting can be sequential or simultaneous. Although many devices can be used for this purpose, one example is a spray dryer. When the precipitator and carrier solution are contacted, the carrier forms a microsphere, incorporating the active agent. In the absence of the active agent, a plain microsphere is formed in which air may be captured.

Microspheres which are targeted to an acidic environment can be made selectively soluble at acidic pH, such as the pH in the stomach. These compositions are prepared with an acid-soluble carrier and a neutral or basic precipitator. The acid-soluble carrier exists largely in the cation form in at least a portion of the pH range from about 1 to about 6.8. However, above about 6.8 or at selected ranges above pH 6.8, the carrier is largely unprotonated and insoluble in water. Therefore, the carrier could self assemble to microspheres at basic or neutral pH.

Microspheres which are to be targeted to an alkaline environment can be made selectively soluble at alkaline pH, such as the pH in the distal portion of the intestine. These compositions are prepared with a base-soluble carrier and a neutral or acidic precipitator. The base-soluble carrier exists largely in an anionic form in at least a portion of the pH range of from about 7.2 to about 11. However, below and at pH 7.2, the carrier is largely protonated and insoluble in water. Therefore, the carrier could self assemble to microspheres at acidic or neutral pH.

Microspheres which are targeted to a neutral environment can be made selectively soluble at neutral pH. These compositions are prepared with a neutral-soluble carrier and an acidic or basic precipitator. The neutral-soluble carrier exists largely in a neutral form at neutral pH, i.e. from about 6.8 to about 7.2. However, above or below this range, the carrier is insoluble in water. Therefore, the carrier could self assemble to microspheres at acidic or basic pH.

In an alternate preferred embodiment of the present application, microsphere formation occurs when the concentration of the acid in an aqueous acid/carrier vehicle is decreased. As this vehicle is nebulized, the acid, if a volatile acid, can evaporate, decreasing the concentration of the acid in solution to less than 30%, and the carrier will self assemble to form microspheres containing any optional active agent. The cargo must be stable in the concentrated acid for the time and conditions necessary to carry out the operation. Alternately, the carrier solution can be diluted, such as with water, whereby the acid concentration is decreased and the carrier precipitates to form microspheres.

Any of the vehicles or solutions or slurries above may optionally contain additives such as stabilizing additives. The presence of such additives promotes the stability and dispersability of the active agent in the vehicle or solution or slurry. The stabilizing additives may be employed at a concentration ranging between about 0.1 and 5% (w/v), preferably about 0.5% (w/v). Suitable, but non-limiting examples of stabilizing additives include buffer salts, gum acacia, gelatin, methyl cellulose, polyethylene glycol, and polylysine.

The amount of active agent which may be incorporated in the microsphere is dependent upon a number of factors which include the concentration of active agent in the carrier and/or precipitator solution as well as the affinity of the active agent for the carrier and/or precipitator. The concentration of the active agent in the final formulation also will vary depending on the required amounts for any particular end use. When necessary, the exact concentration can be determined by, for example, reverse phase HPLC analysis.

The microspheres and, therefore, the vehicles described above may also include one or more enzyme inhibitors. Such enzyme inhibitors include, but are not limited to, compounds such as actinonin or epiactinonin and derivatives thereof.

The microspheres are particularly useful for administering biologically active agents to any animals such as birds; mammals, such as primates and particularly humans; and insects. The system is particularly advantageous for delivering chemical or biologically active agents which would otherwise be destroyed or rendered less effective by conditions encountered before the microsphere reaches the active agent target zone (i.e., the area in which the active agent of the delivery composition are to be released) and within the body of the animal to which they are administered. Particularly, the compositions of the present invention are useful in orally administering active agents, especially those which are not ordinarily orally deliverable. Additionally, microspheres without an active agent are useful for contrast imaging, such as ultrasound imaging.

Spray Driving Apparatus

The process of nebulizing and contacting the carrier solution and the precipitator solution may be conveniently conducted utilizing one or more spray nozzles.

The carrier solution or slurry, which may contain the active ingredient, and the precipitator, which alternatively may contain the active ingredient, are delivered under pressure to the spray nozzle(s). The carrier solution or slurry and the precipitator are then nebulized, with a pressurized gas, outside the orifice of the spray nozzle(s) to produce an atomized mist. The carrier and the precipitator combine in the atomized mist to produce microspheres which may then be further treated or stored as desired.

FIG. 2 illustrates one embodiment of an apparatus 10. Reservoirs 11 and 13 which contain a solution or slurry of a carrier 12 and a precipitator 14, respectively. The carrier solution, the precipitator, or both may contain the active agent, which is preferably a biologically or chemically active agent. Other reservoirs (not shown) may be provided if other materials are to be added.

The carrier solution or slurry 12 and the precipitator 14 flow through pumps 15, such as for example, variable speed peristaltic pumps. After exiting the pumps, the pressurized solutions 12 and 14 are delivered to a spray nozzle 17. A compressor unit 16 supplies a pressurized gas, preferably air, to the spray nozzle 17. The temperatures of the materials delivered to the nozzle may be controlled by one or more heat exchangers (not shown). When the carrier solution or slurry 12, the precipitator 14, and the pressurized gas reach the tip of the outlet 18 of the spray nozzle 17, the carrier solution or slurry and the precipitator are instantaneously nebulized into a fine mist 19. The contact of the carrier solution and the precipitator results in a precipitated microsphere in chamber 20 which optionally contain the active agent. These particles are instantaneously dried in a warm air stream provided by heater 22 and blower 23. The microspheres may be collected in a collection reservoir 21 for further processing.

A preferred multi-path spray nozzle configuration is illustrated in FIG. 3. The spray nozzle 22 includes a first delivery pipe 23 for delivering a carrier solution 12 to a nozzle outlet 27. The first pipe has an inlet portion for incoming carrier solution and an outlet portion for exiting carrier solution. The outlet portion is in open communication with the nozzle outlet 27. A second delivery pipe 25, which is preferably coaxially arranged around the first delivery pipe 23 and substantially the same length as the first delivery pipe 23, is employed to deliver the precipitator 14 to the nozzle outlet 27. The second delivery pipe also has an inlet portion and an outlet portion, the outlet portion being in open communication with the nozzle outlet. Additional coaxially arranged pipes (not shown) may be utilized if desired to additional components to the spray nozzle 22. A pressurized gas delivery jacket 26, preferably tapered having inlet and outlet portions, surrounds the first and second delivery pipe outlet portions but not the nozzle outlet. This jacket delivers a pressurized gas, preferably air, to the spray nozzle 22. The pressurized gas is ejected from an annular region 27 between the air jacket 26 and the outer pipe 25. When the carrier solution 12, the precipitator 14, and the compressed gas reach the nozzle outlet 22, the carrier solution and the precipitator are forcefully ejected from the nozzle outlet 22 and nebulized outside the nozzle outlet. The contact of the carrier solution and the precipitator results in the precipitation of microspheres 20 which optionally contain the active agent.

Heated air is blown across the nebulized stream, resulting in rapid evaporation of any volatile components. This leaves a dry powder which is swept to a collector where it is captured for use.

Pressures, feed rates, blower speeds, operating temperatures and other operating conditions can be determined by those skilled in the art. Typically, delivery pressures for the solutions will need air from about 0.2 ml/min. to about 15 ml/min., and temperature of the needed air will range from about 80° C. to about 180° C.

DESCRIPTION OF THE PREFERRED EMBODIMENTS

Figure 1A:
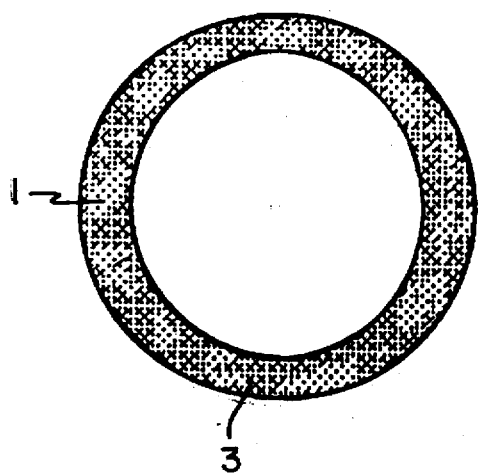
Figure 1B:
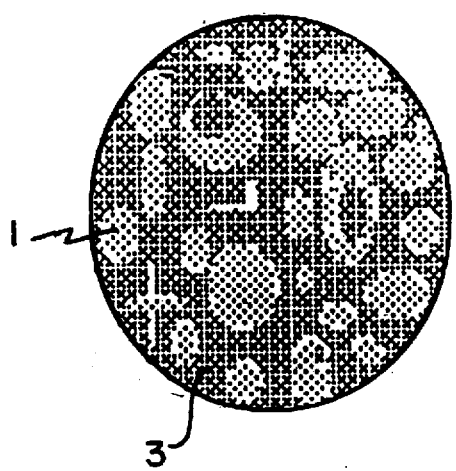
Figure 1C:
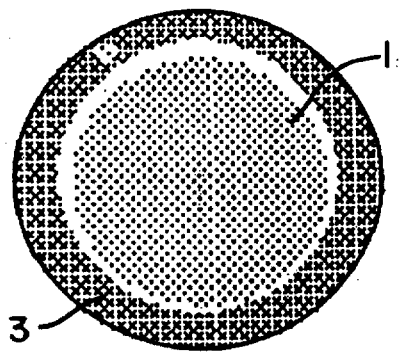
Figure 1D:
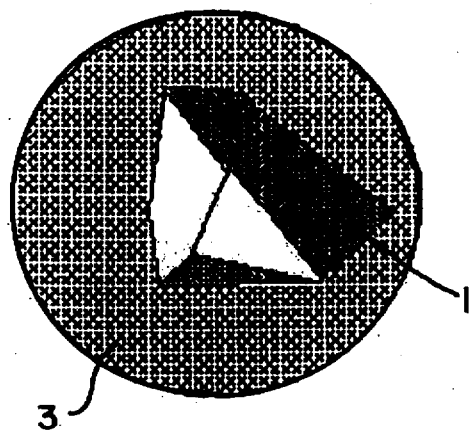
Figure 2:
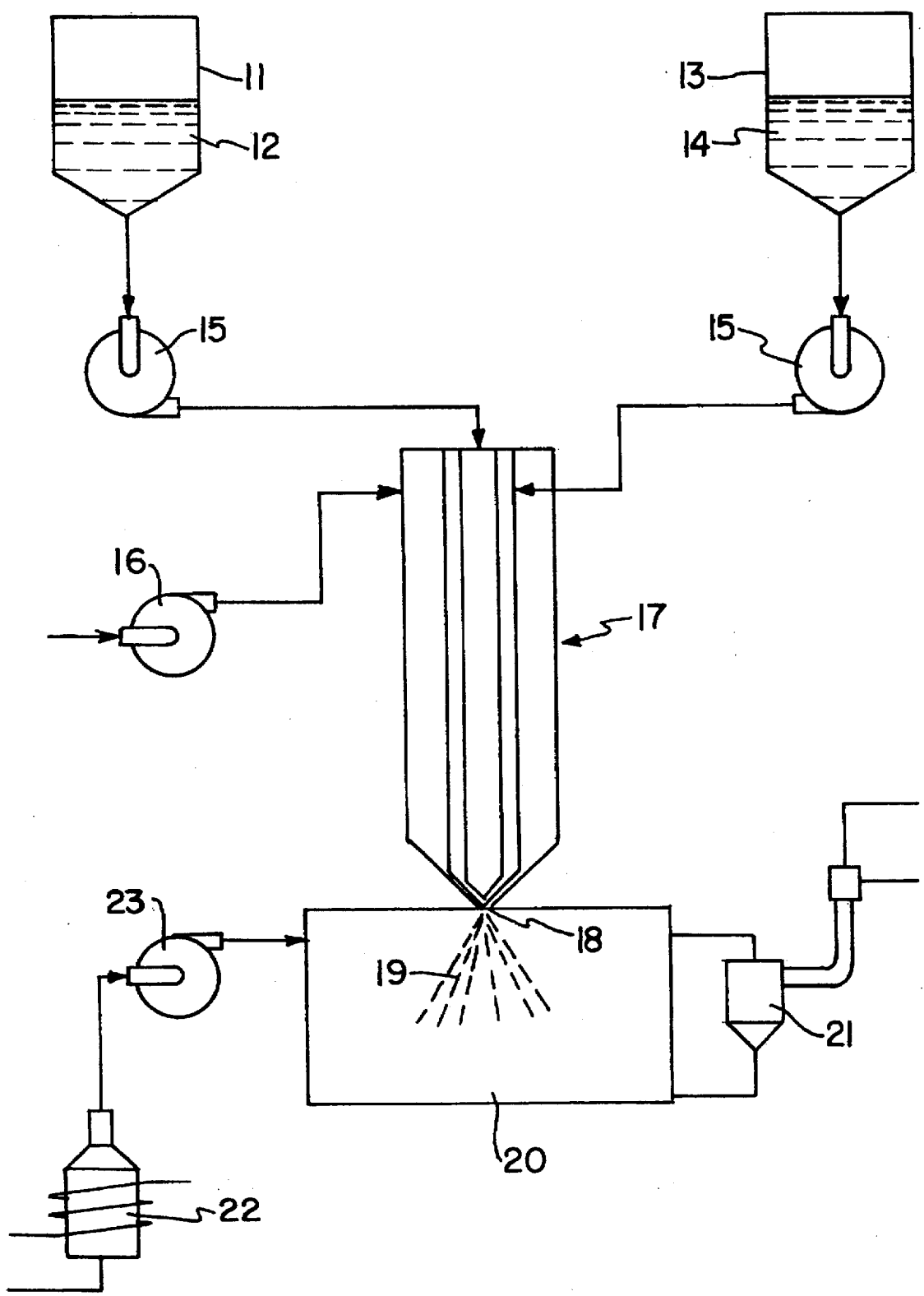
Figure 3:
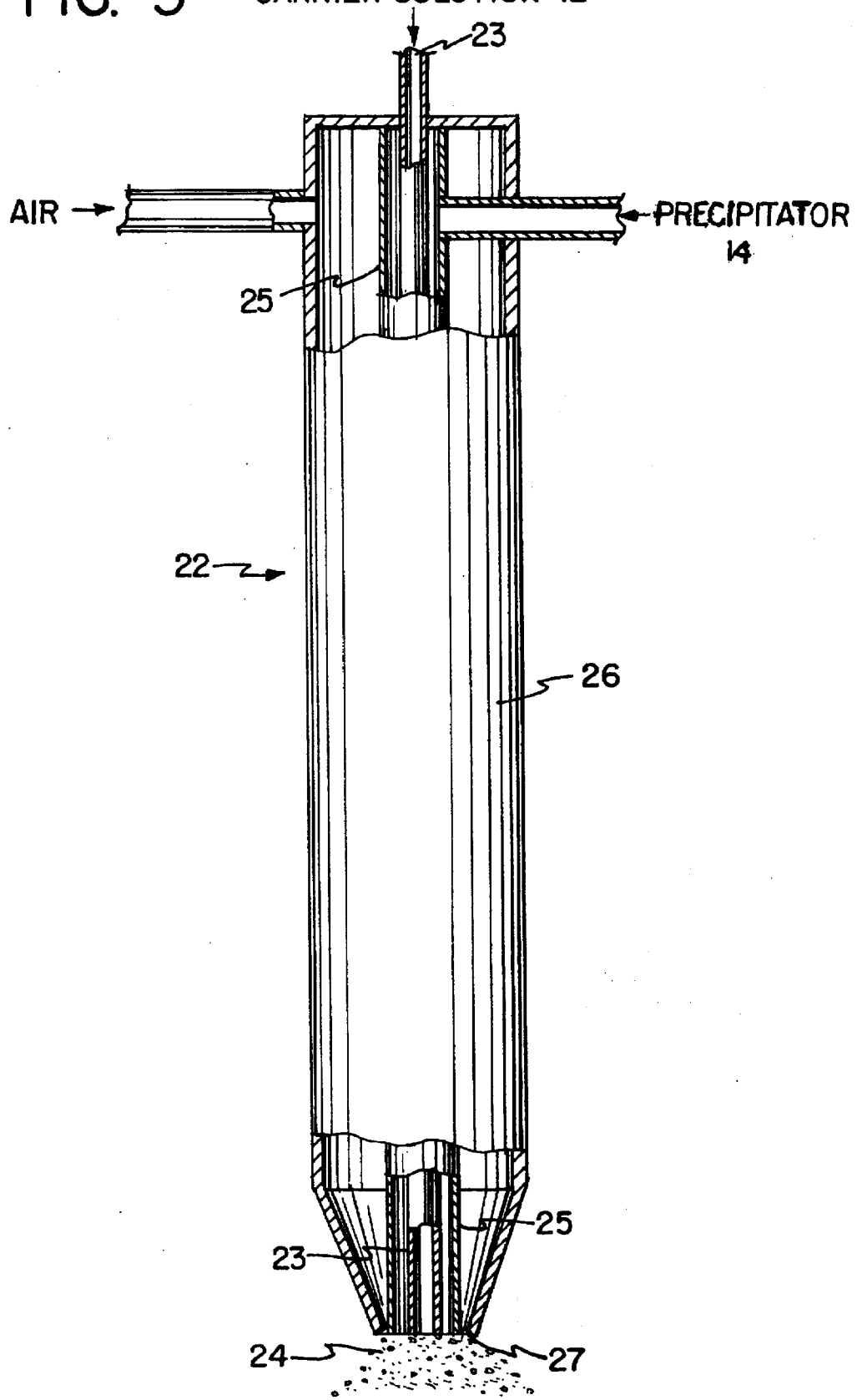

The following Examples illustrate the present invention without limitation.

EXAMPLE 1

PROTEINOID CARRIER SOLUTION/ PRECIPITATOR 10 grams of proteinoid (Glu-Asp-Tyr-Phe-Orn) were slurried in 125 ml of water. 3 ml of ammonium hydroxide were added to the slurry, and the mixture was stirred until the proteinoid dissolved. This carrier solution was then filtered to remove particulates.

4.4 grams of citric acid were dissolved with stirring in 125 ml of water. 2.5 grams of heparin were added and stirring continued until dissolution was complete, yielding a precipitator solution.

Using peristaltic feed pumps, the carrier solution was fed through an outer conduit and the heparin precipitator solution was fed through an inner conduit of a modified spray nozzle with a spray drying apparatus (Virtis SD04).

Spray drier conditions are described in Table 1.

TABLE 1

| SPRAY DRYING CONDITIONS | |
|---|---|
| Carrier Solution Flow Rate | 5 ml/min |
| Precipitator Solution Flow Rate | 5 ml/min |
| Inlet Temperature | 175° C. |
| Outlet Temperature | 110° C. |
| Blower Speed | full |
| Compressor Pressure | full |

The carrier solution and precipitator solution were simultaneously contacted, nebulized, and dried to form stable proteinoid microspheres containing heparin.

EXAMPLE 2

PROTEINOID CARRIER SOLUTION/ PRECIPITATOR 10 grams of proteinoid (Glu-Asp-Tyr-Phe) were slurried in 100 ml of water. Sodium bicarbonate was added to solubilize the proteinoid and to adjust the pH of this carrier solution to 7. The carrier solution was filtered to remove particulates.

0.1 gram of surfactant (Tween 80) was dissolved in 100 ml of water, and 3.5 grams of finely powdered itraconazole were slurried in 10 ml of isopropanol. The itraconazole slurry was added, with agitation, to the Tween solution. 2 grams of citric acid were added with stirring, yielding a precipitator solution.

The carrier and precipitator solutions were simultaneously contacted and nebulized with the apparatus described in Example 1 and under the conditions in Table 2 to form stable proteinoid microspheres containing itraconazole.

TABLE 2

| SPRAY DRYING CONDITIONS | |
|---|---|
| Carrier Solution Flow Rate | 5 ml/min |
| Itraconazole/Precipitator Solution | 5 ml/min |
| Inlet Temperature | 175° C. |
| Outlet Temperature | 100° C. |
| Nebulizing Air | 90° C. |
| Blower Speed | full |

EXAMPLE 3

PROTEINOID CARRIER SOLUTION/ PRECIPITATOR 10 grams of proteinoid (Glu-Asp-Tyr-Phe-Orn) were slurried in 100 ml of water. Ammonium hydroxide was added dropwise with stirring until the proteinoid dissolved. This carrier solution was filtered to remove particulates.

2.5 grams of citric acid were dissolved in 100 ml water. 40 mg of insulin were added and stirred until dissolved to yield a precipitator solution.

The solutions were simultaneously nebulized and contacted with the apparatus described in Example 1 and under the conditions described in Table 3 to form stable microspheres containing insulin.

TABLE 3

| SPRAY DRYING CONDITIONS | |
|---|---|
| Solution Flow Rate | 5 ml/min |
| Insulin/Precipitation Solution | 5 ml/min |
| Inlet Temperature | 175° C. |
| Outlet Temperature | 103° C. |

EXAMPLE 4

PROTEINOID CARRIER SOLUTION/ EVAPORATION 200 ml of water and 100 ml of glacial acetic acid were mixed. 6 grams of proteinoid (Glu-Asp-Tyr-Phe-Orn) were added, and the mixture stirred until dissolved. 3 grams of heparin were added, and the mixture was stirred until the heparin dissolved. The solution was filtered to remove particulates. The solution was nebulized with a spray drying apparatus having a conventional spray nozzle under the conditions in Table 4 to form stable proteinoid microspheres containing heparin.

TABLE 4

| SPRAY DRYING CONDITIONS | |
|---|---|
| Feed Rate | 7 ml/min |
| Inlet Temperature | 125° C. |
| Outlet Temperature | 80° C. |
| Blower Speed | 1.25 turns |
| Compressor Pressure | 70 |

EXAMPLE 5

ENTERIC COATING CARRIER/EVAPORATION 10 grams of cellulose acetate trimellitate were dissolved, with stirring and warming, in 500 ml of a 60% acetic acid solution. 5 grams of heparin were added, and stirring was continued until dissolution was complete.

The solution was nebulized and dried with a spray drying apparatus as described in Example 3 and under the conditions of Table 5 to form stable microspheres containing heparin.

TABLE 5

| SPRAY DRYING CONDITIONS | |
| --- | --- |
| Feed Rate | 5 ml/min |
| Inlet Temperature | 115° C. |
| Outlet Temperature | 75° C. |
| Blower | 100 |
| Compressor | 8.5 |

Stable proteinoid microspheres containing heparin were prepared.

All patents, applications, publications, and test methods mentioned herein are hereby incorporated by reference in their entirety.

Many variations of the present invention will suggest themselves to those skilled in the art in light of the above detailed description in which obvious variations are within the full intended scope of the appended claims.

I claim:

1. A method for preparing microspheres, said method comprising:
    (A) nebulizing each of
        (a) a carrier vehicle comprising a microsphere forming carrier; and
        (b) a precipitator;
        wherein said carrier vehicle (a) or said precipitator (b) optionally includes an active agent; and
    (B) contacting said carrier vehicle and said precipitator.

2. A method as defined in claim 1, when (A) and (B) are performed simultaneously.

3. A method as defined in claim 1, wherein said microspheres comprise microcapsules.

4. A method as defined in claim 1, wherein said contacting and nebulizing is performed by spray drying.

5. A method as defined in claim 1, wherein said carrier vehicle comprises a solution.

6. A method as defined in claim 5, wherein said carrier solution comprises a neutral solution.

7. A method as defined in claim 1, wherein said carrier vehicle comprises a slurry.

8. A method as defined in claim 1, wherein said carrier vehicle is selected from the group consisting of
   (i) a proteinoid;
   (ii) an acylated amino acid or poly amino acid or a salt thereof;
   (iii) a sulfonated amino acid or poly amino acid or a salt thereof;
   (iv) a protein or a salt thereof;
   (v) an enteric coating material; and
   (vi) any combination thereof.

9. A method as defined in claim 5, wherein said carrier vehicle further comprises water.

10. A method as defined in claim 1, wherein said carrier vehicle comprises a proteinoid.

11. A method as defined in claim 1, wherein said carrier comprises an acylated amino acid or poly amino acid or a salt thereof.

12. A method as defined in claim 1, wherein said carrier which comprises a sulfonated amino acid or poly amino acid or a salt thereof.

13. A method as defined in claim 1, wherein said carrier which comprises a protein or a salt thereof.

14. A method as defined in claim 1, wherein said carrier which comprises an enteric coating material.

15. A method as defined in claim 14, wherein said enteric coating material is selected from the group consisting of cellulose acetate trimellitate, cellulose acetate phthalate, and a combination thereof.

16. A method as defined in claim 1, wherein said carrier vehicle further comprises said active agent.

17. A method as defined in claim 1, wherein said precipitator comprises an acidic solution.

18. A method as defined in claim 1, wherein said precipitator further comprises said active agent.

19. A method as defined in claim 1, wherein said active agent comprise a biologically active agent.

20. A method as defined in claim 19, wherein said biologically active agent comprises a pharmacologically active agent.

21. A method as defined in claim 1, wherein said active agent comprises a chemically active agent vehicle.

22. A method as defined in claim 1, wherein said microspheres have an average diameter of less than about 10 microns.

23. A method for preparing microspheres, said method comprising:
   (A) nebulizing an aqueous acid/carrier solution comprising
      (a) a volatile acid;
      (b) a microsphere forming carrier; and
      (c) optionally an active agent;
         wherein the volume:volume ratio of acid to water in said carrier solution is at least about 3:7; and
   (B) decreasing said ratio to less than about 3:7, to yield said microspheres.

24. A method for preparing active agent containing microspheres, said method comprising:
   (A) nebulizing an aqueous acid/carrier solution comprising
      (a) a volatile acid;
      (b) a carrier comprising a member selected from the group consisting of
         (i) a proteinoid,
         (ii) an acylated amino acid or poly amino acid or a salt thereof,
         (iii) a sulfonated amino acid or poly amino acid or a salt thereof,
         (iv) a protein or a salt thereof,
         (v) an enteric coating material, and
         (vi) any combination thereof, and
      (c) an active agent;
         wherein the volume:volume ratio of acid to water in said carrier solution is at least about 3:7; and
   (B) decreasing said ratio to less than about 3:7, to yield said microspheres.

25. A method as defined in claim 23, wherein said nebulizing is performed by spray drying.

26. A method as defined in claim 23, wherein said acid comprises acetic acid.

27. A method as defined in claim 23, wherein said carrier comprises a proteinoid.

28. A method as defined in claim 23, wherein said carrier comprises an acylated amino acid or poly amino acid or a salt thereof.

29. A method as defined in claim 23, wherein said carrier comprises a sulfonated amino acid or poly amino acid or a salt thereof.

30. A method as defined in claim 23, wherein said carrier comprises a protein or a salt thereof.

31. A method as defined in claim 23, wherein said carrier comprises an enteric coating material.

32. A method as defined in claim 23, wherein said active agent comprises a biologically active agent.

33. A method as defined in claim 32, wherein said biologically active agent comprises a pharmaceutically active agent.

34. A method as defined in claim 23, wherein said active agent comprises a chemically active agent.

35. A method as defined in claim 23, wherein said microspheres have an average diameter of less than about 10 microns.

36. A method as defined in claim 23, wherein said ratio is decreased by volatilizing at least a portion of said acid.

37. A method as defined in claim 23, wherein said ratio is decreased by diluting said acid.

38. A method for preparing active agent containing microspheres, said method comprising
 (A) providing a spray nozzle comprising;
  (a) a first delivery pipe having an inlet portion and an outlet portion, said first pipe outlet portion in open communication with a nozzle outlet;
  (b) a second delivery pipe, said second pipe having an inlet and an outlet portion, said second pipe outlet portion in open communication with said nozzle outlet; and
  (c) a pressurized gas delivery jacket having an inlet portion and an outlet portion, said jacket outlet portion surrounding both said first and said second pipe outlet portions but not said nozzle outlet, and in open communication with said nozzle outlet;
 (B) delivering to said first delivery pipe inlet portion, a carrier vehicle comprising a carrier selected from the group consisting of
  (a) a proteinoid,
  (b) an acylated amino acid or poly amino acid or a salt thereof,
  (c) a sulfonated amino acid or poly amino acid or a salt thereof,
  (d) a protein or a salt thereof,
  (e) an enteric coating material, and
  (f) any combination thereof;
 (C) delivering a precipitator to said second delivery pipe inlet portion;
 (D) delivering pressurized air to said jacket; and
 (E) simultaneously nebulizing and contacting said carrier vehicle and said precipitator; wherein said carrier vehicle or said precipitator includes said active agent.

* * * * *